(12) United States Patent
Ching et al.

(10) Patent No.: US 6,510,722 B1
(45) Date of Patent: Jan. 28, 2003

(54) STENT CRIMPING TOOL FOR PRODUCING A GROOVED CRIMP

(75) Inventors: Denise Ching, San Jose, CA (US); Matthew J. Gillick, Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/568,273

(22) Filed: May 10, 2000

(51) Int. Cl.$^7$ ................................................ B21D 39/00
(52) U.S. Cl. ................................ 72/402; 29/282; 606/1
(58) Field of Search ............................ 72/402; 29/282; 606/1

(56) References Cited

U.S. PATENT DOCUMENTS

| | | |
|---|---|---|
| 141,992 A | 8/1873 | Carr |
| 579,214 A | 3/1897 | Adams |
| 696,289 A | 3/1902 | Williams |
| 852,290 A | 4/1907 | Neal |
| 915,184 A | 3/1909 | Keirn |
| 1,045,886 A | 12/1912 | Reay |
| 1,230,561 A | 6/1917 | Chige |
| 1,268,171 A | 6/1918 | Spaulding |
| 1,758,261 A | 5/1930 | Leland |
| 1,966,593 A | 1/1934 | O'Russa |
| 2,452,857 A | 11/1948 | Mesaros |
| 2,465,433 A | 3/1949 | Doniger |
| 2,553,479 A | 5/1951 | Schrmarge et al. |
| 3,496,684 A | 2/1970 | Banning et al. |
| 3,898,897 A | 8/1975 | Jauhianinen |
| 3,977,065 A * | 8/1976 | Johnson ........................ 72/402 |
| 4,041,766 A * | 8/1977 | Johnson ........................ 72/402 |
| 4,107,964 A | 8/1978 | Smith |
| 4,215,871 A | 8/1980 | Hirsch et al. |
| 4,468,224 A | 8/1984 | Enzmann et al. |
| 4,567,650 A * | 2/1986 | Balyasny ...................... 72/402 |
| 4,576,142 A | 3/1986 | Schiff |
| 4,644,936 A | 2/1987 | Schiff |
| 4,681,092 A | 7/1987 | Cho et al. |

(List continued on next page.)

FOREIGN PATENT DOCUMENTS

| | | |
|---|---|---|
| CA | 2211694 | 2/1998 |
| DE | 297 14 857 U | 11/1997 |
| EP | 303 889 A2 | 2/1989 |
| EP | 303 889 B1 | 2/1989 |
| EP | 0 630 623 A2 | 12/1994 |
| EP | 0 630 623 A3 | 12/1994 |
| EP | 562 478 A1 | 1/1996 |
| EP | 0 826 246 A1 | 3/1998 |
| EP | 0 873 731 A1 | 10/1998 |
| EP | 938 880 A2 | 9/1999 |
| FR | 975 797 A | 3/1951 |
| GB | 159065 | 2/1921 |
| GB | 2 088 811 A | 6/1982 |
| WO | WO 97/09946 | 3/1997 |
| WO | WO 98/14120 | 4/1998 |
| WO | WO 98/19633 | 5/1998 |

OTHER PUBLICATIONS

C.R. Bard Brochure, The Extraordinary Stent (Undated).

*Primary Examiner*—Daniel C. Crane
(74) *Attorney, Agent, or Firm*—Fulwider Patton Lee & Utecht, LLP (57) ABSTRACT

A crimping device for crimping a stent onto the inflation balloon of a stent delivery catheter. The device forms a crimp which creates regions of high frictional resistance between the stent and the inflation balloon. In one form, the crimp comprises a plurality of spaced grooves running the longitudinal length of the stent. In another form, the crimp is composed of a plurality of radial indentations spaced along the body of the stent. The device including an inner hub housing a plurality of radially spaced crimping jaws and an outer hub enclosing the jaws. The outer hub being rotatably connected to the inner hub and including means for forcing the jaws to move radially inwardly to crimp a stent.

20 Claims, 5 Drawing Sheets

U.S. PATENT DOCUMENTS

| | | |
|---|---|---|
| 4,697,573 A | 10/1987 | Schiff |
| 4,901,707 A | 2/1990 | Schiff |
| 4,907,336 A | 3/1990 | Gianturco |
| 4,987,722 A | 1/1991 | Koebbeman |
| 5,132,066 A | 7/1992 | Charlesworth et al. |
| 5,133,732 A | 7/1992 | Wiktor |
| 5,183,085 A | 2/1993 | Timmermans |
| 5,189,786 A | 3/1993 | Ishikawa et al. |
| 5,195,539 A | 3/1993 | Dryud et al. |
| 5,209,143 A | 5/1993 | Sweet |
| 5,217,434 A | 6/1993 | Arney |
| 5,437,083 A | 8/1995 | Williams et al. |
| 5,456,667 A | 10/1995 | Ham et al. |
| 5,458,615 A | 10/1995 | Klemm et al. |
| 5,476,505 A | 12/1995 | Limon |
| 5,540,124 A | 7/1996 | Srhoj |
| 5,546,646 A | 8/1996 | Williams et al. |
| 5,626,604 A | 5/1997 | Cottone, Jr. |
| 5,630,830 A | 5/1997 | Verbeek |
| 5,653,691 A | 8/1997 | Rupp et al. |
| 5,672,169 A | 9/1997 | Verbeek |
| 5,695,515 A | 12/1997 | Orejola |
| 5,715,723 A | 2/1998 | Owens |
| 5,725,519 A | 3/1998 | Penner et al. |
| 5,738,674 A | 4/1998 | Williams et al. |
| 5,746,764 A | 5/1998 | Green et al. |
| 5,783,227 A | 7/1998 | Dunham |
| 5,785,715 A | 7/1998 | Schatz |
| 5,795,289 A | 8/1998 | Wyttenbach |
| 5,810,838 A | 9/1998 | Solar |
| 5,810,873 A | 9/1998 | Morales |
| 5,836,952 A | 11/1998 | Davis et al. |
| 5,860,966 A | 1/1999 | Tower |
| 5,893,852 A | 4/1999 | Morales |
| 5,893,867 A | 4/1999 | Bagaoisan et al. |
| 5,911,452 A | 6/1999 | Yan |
| 5,920,975 A | 7/1999 | Morales |
| 5,938,696 A | 8/1999 | Goicoechea et al. |
| 5,951,540 A * | 9/1999 | Verbeck ......................... 606/1 |
| 5,972,016 A | 10/1999 | Morales |
| 5,974,652 A | 11/1999 | Kimes et al. |
| 6,009,614 A | 1/2000 | Morales |
| 6,024,737 A | 2/2000 | Morales |
| 6,063,102 A | 5/2000 | Morales |
| 6,082,990 A | 7/2000 | Jackson et al. |
| 6,092,273 A | 7/2000 | Villareal |
| 6,167,605 B1 * | 1/2001 | Morales .................... 29/282 |
| 6,171,327 B1 | 1/2001 | Daniel et al. ............... 606/200 |
| 6,179,859 B1 | 1/2001 | Bates et al. ................. 606/200 |

* cited by examiner

STENT CRIMPING TOOL FOR PRODUCING A GROOVED CRIMP

BACKGROUND OF THE INVENTION

The present invention relates to the field of stent crimping devices generally, and more particularly, to a device for providing a grooved crimp which is generally parallel to the axis of a stent.

Stents are typically used as adjuncts to percutaneous transluminal balloon angioplasty procedures in the treatment of occluded or partially occluded arteries and other blood vessels. In a typical balloon angioplasty procedure, a guiding catheter or sheath is percutaneously introduced into the cardiovascular system of a patient through the femoral arteries and advanced through the vasculature until the distal end of the guiding catheter is positioned at a point proximal to the lesion site. A guide wire and a dilatation catheter having a balloon on the distal end are introduced through the guiding catheter with the guide wire sliding within the dilatation catheter. The guide wire is first advanced out of the guiding catheter into the patient's vasculature and is directed across the arterial lesion. The dilatation catheter is subsequently advanced over the previously advanced guide wire until the dilatation balloon is properly positioned across the arterial lesion. Once in position across the lesion, the expandable balloon is inflated to a predetermined size with a radiopaque liquid at relatively high pressure to radially compress the atherosclerotic plaque of the lesion and increase the diameter of the occluded artery. The balloon is then deflated to a small profile so that the dilatation catheter can be withdrawn from the patient's vasculature and blood flow resumed through the dilated artery. As will be appreciated by those skilled in the art, while the above-described procedure is typical, it is not the only method used in angioplasty.

Balloon angioplasty sometimes results in short or long term failure. Vessels may collapse abruptly shortly after the procedure or a gradual narrowing of the vessel (restenosis) may occur for several months thereafter. To counter the tendency of recurrent vessel occlusion following angioplasty, implantable intravascular prostheses, commonly referred to as stents, have emerged as a means by which to achieve long term vessel patency. A stent functions as permanent scaffolding to structurally support the vessel wall and thereby maintain lumen patency. Stents are typically small expandable cylindrically-shaped devices which have a generally open cellular construction. Stents usually are transported to a lesion site by means of a delivery catheter.

There are two general classes of stents namely, balloon expandable stents and self-expandable stents. Balloon expandable stents are delivered in a small diameter or low profile configuration by means of a balloon catheter and are plastically deformed to a second larger diameter by means of an inflation balloon. Self-expanding stents are formed as spring elements which are radially compressible about a delivery catheter. A self-expanding stent is typically held in the compressed state by a delivery sheath. Upon delivery to a lesion site, the delivery sheath is retracted allowing the stent to expand.

Details of balloon expandable stents can be found in U.S. Pat. No. 5,514,154 (Lau, et al.); U.S. Pat. No. 5,421,955 (Lau et al.); U.S. Pat. No. 5,603,721 (Lau et al.); U.S. Pat. No. 4,733,665 (Palmaz); No. 4,739,762 (Palmaz); and U.S. Pat. No. 5,569,295 (Lam). These patents describe a few typical examples of the more common types of balloon expandable stents. There are many other designs which have been developed.

Stent crimping devices often are used to secure balloon expandable stents to the inflation balloons of stent-delivery catheters. A stent is first loaded and then crimped onto the balloon portion of a stent delivery catheter. The stent-delivery catheter is advanced to a position where the stent crosses the arterial lesion. The balloon is inflated causing the stent to expand to its deployed diameter for implantation in the artery wall. To ensure proper deployment, the stent must be securely mounted on the balloon portion of the delivery catheter. If the stent should slip on the balloon during delivery, nonuniform deployment may result. In this situation, the stent may partially occlude the artery, thereby worsening the condition that the stent is intended to repair. Occasionally, stents have slid completely off of the balloon and have migrated downstream in the patient's artery, sometimes necessitating emergency removal procedures. Thus, the problem of stent slippage on delivery catheters is a serious concern to vascular surgeons.

In the past, stents have been crimped onto catheter balloons by hand, often with the aid of small tools such as sterile pliers, or by machines built specifically for crimping. Many prior art devices have been directed towards achieving what is referred to as a "roll crimp" of the stent onto the balloon, i.e., the stent is uniformly compressed about the balloon portion of the delivery catheter. Problems commonly associated with hand-crimping include non-uniform crimping, the inability to determine if a reliable crimp has been achieved, and physical damage to the stent which can be easily overlooked by visual inspection and can cause the stent to expand improperly within the patient.

Several devices have been developed in an attempt to address these problems. One such device is described in U.S. Pat. No. 5,437,083, entitled "Stent Loading Mechanism," issued to Williams et. al, Aug. 1, 1995. The Williams device utilizes a series of plates which have substantially flat and parallel surfaces that move in a rectilinear fashion with respect to each other. A stent is slipped over the balloon portion of the delivery catheter and the strut is placed between these surfaces. The stent is roll crimped onto the balloon by relative motion of the plates. The Williams device has been successful in producing a uniform roll crimp.

Machine crimped stents with roll type crimps have proven to be reliable as well. However, in certain circumstances, such as when the stent encounters obstacles such as hardened plaque or a flap of tissue partially torn from a vessel wall, roll crimped stents occasionally will still move or slide off of the delivery catheter. It is believed that this slippage problem may continue to occur because a stent uniformly crimped along its length forms a somewhat smooth continuous interface with the balloon and may not always generate sufficient frictional resistance to remain positioned on the balloon, especially when subjected to external forces created when delivering the stent within the patient's vasculature.

Typical materials used for the balloon portion of a delivery catheter include polyester, polyamide, and polyolefin, all of which usually exhibit a relatively low coefficient of friction, when bearing against a metallic structure such as a stainless steel stent. Therefore, in situations where maximum stent security is required, what is needed is a stent crimping device that will create regions of high frictional resistance between the stent and the balloon, thereby improving stent security on the balloon.

SUMMARY OF THE INVENTION

The stent crimping device of the present invention has three main components, an inner hub, an outer hub, and a plurality of radially inwardly sliding jaws which engage the stent. The inner hub includes means for retaining the sliding jaws and also includes spring-loaded push rod assemblies which bias the jaws radially outwardly to an open position. Each jaw includes a crimping surface for forming a selected type of crimp. The crimping surface may have several profiles including, but not limited to, V-shaped, U-shaped, and flat surfaces. The outer hub is rotatably engaged over the inner hub and encloses the sliding jaws. The outer hub includes an opening which guides and centers the stent-delivery catheter between the sliding jaws. Rotation of the outer hub causes the slidable jaws to move radially inwardly so that the jaws engage and securely crimp a stent to the expandable member of the stent-delivery catheter. Rotation of the outer hub in the reverse direction allows the spring-loaded push rods to bias the jaws radially outwardly thereby releasing the crimped stent. The stent crimping device may be used for on-site crimping of stents to delivery catheters at a medical facility or may be readily adapted for mass production of pre-crimped stent-delivery catheter assemblies.

The crimping device of the present invention can provide at least two general types of stent crimps. In one form, the stent crimp is composed of a plurality of spaced grooves which run the longitudinal length of the stent. The number and spacing of the grooves will vary depending on the size and type of stent. In a second form, the stent crimp is composed of a plurality of radial indentations spaced along the body of the stent. The spacing of the indentations may vary both radially around the circumference of the stent and longitudinally along the length of the stent. Both the grooved type crimp and the radial-indentation type crimp deform the stent so that it engages the balloon material to create regions of high frictional resistance between the metal struts of the stent and the expandable member of the stent delivery catheter. The regions of high frictional resistance created by the crimping device generally affix the stent to the balloon more securely than a roll type crimp.

Other features and advantages of the present invention will become more apparent from the following detailed description of the invention, when taken in conjunction with the accompanying exemplary drawings.

DETAILED DESCRIPTION OF THE PREFERRED EMBODIMENTS

Figure 1:
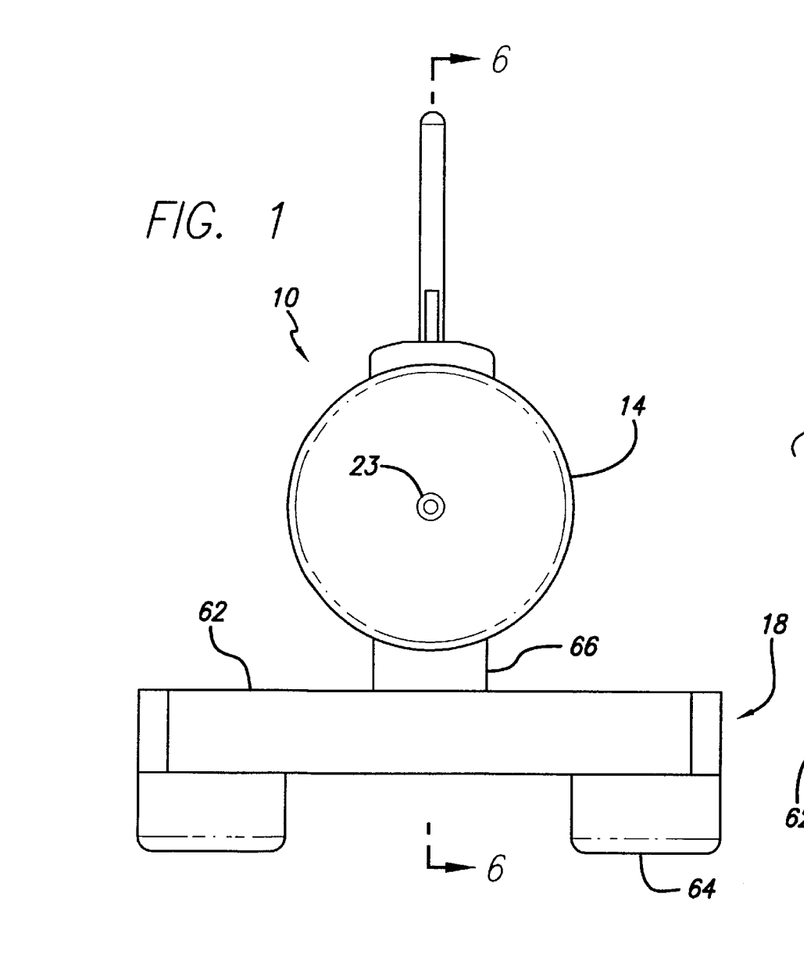
FIG. 1 is a front view of a stent crimping device embodying features of the present invention.
Figure 2:
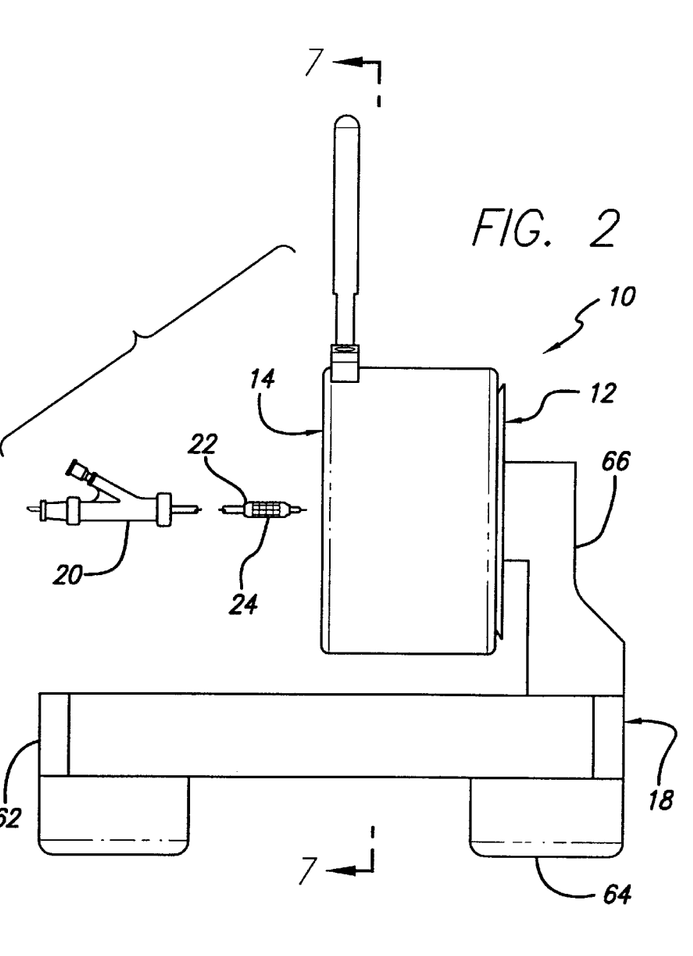
FIG. 2 is a side view of the stent crimping device shown in FIG. 1.
Figure 3:
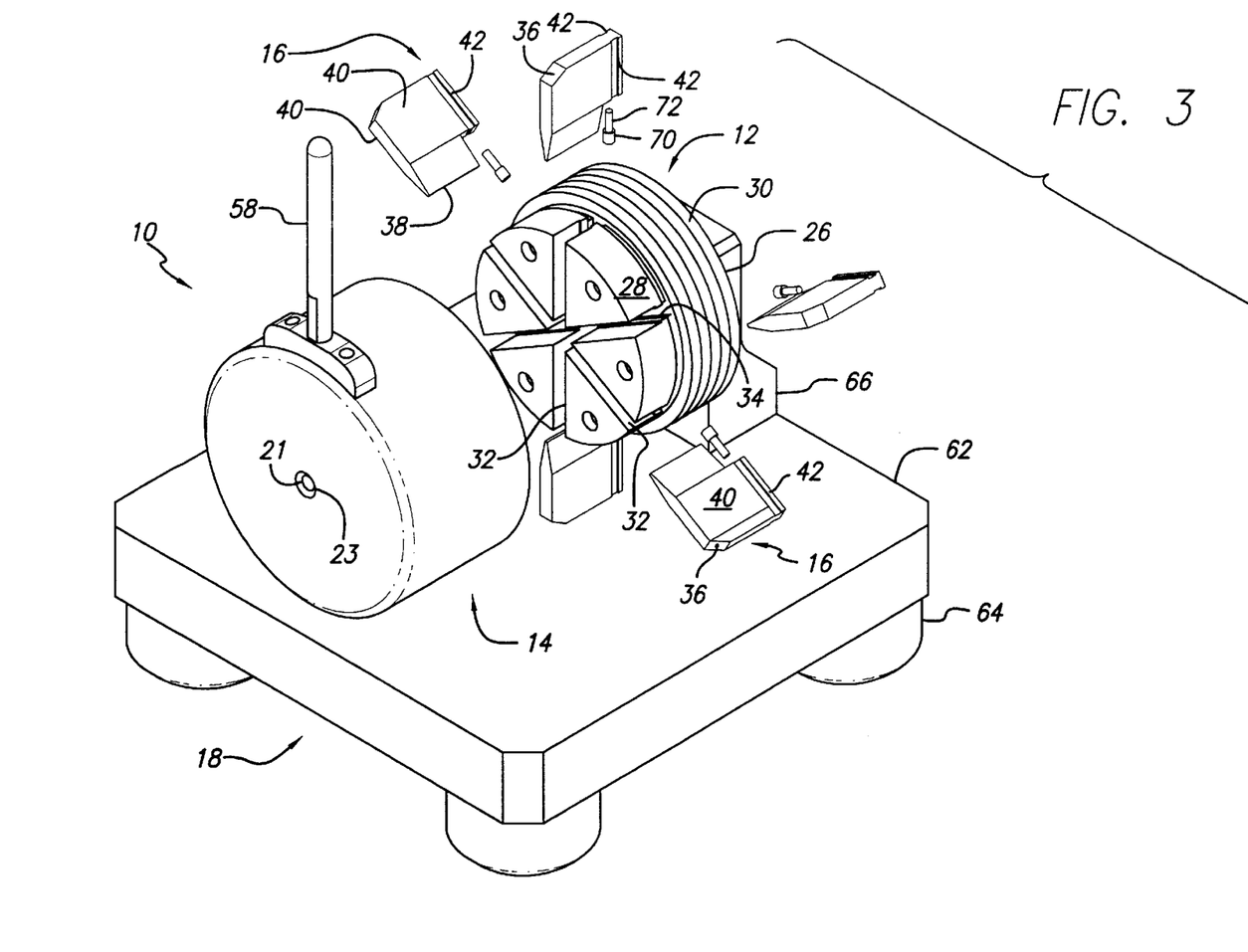
FIG. 3 is an exploded view, enlarged in scale, of the stent crimping device of FIGS. 1 and 2.

FIGS. 1–3, illustrate a sent crimping device 10 embodying features of the present invention. The stent crimping device includes an inner hub 12, an outer hub 14, a plurality of crimping jaws 16, and a base assembly 18. A stent delivery system, such as the stent-delivery catheter 20, having an expandable member (shown herein as an inflatable balloon 22) which is loaded with a stent 24 to be crimped, can be inserted into the device 10 through an aperture 23.

Referring now to FIG. 3, the primary features of each major component are as follows. The inner hub 12 includes a cylindrical disk portion 26 and a plurality of slide blocks 28 which may be integrally formed with the inner hub 12 or may be formed as component parts which are attached to the inner hub 12. The cylindrical disk portion 26 includes an external power screw thread 30. Each slide block 28 includes opposing bearing faces 32. Each bearing face includes a guide rail 34. The slide blocks 28 are spaced about the cylindrical disk portion 26 of the inner hub 12 such that the crimping jaws 16 may be slidably received between each adjacent slide block 28.

Figure 4:
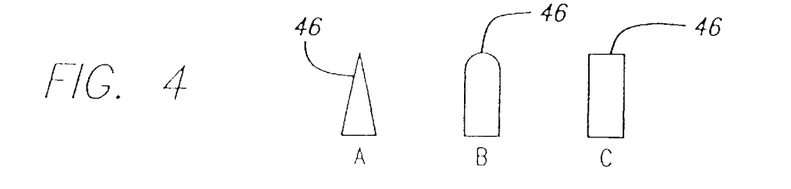
FIG. 4A shows one embodiment of a front profile of a crimping jaw in accordance with the present invention.
FIG. 4B shows a second embodiment of a front profile of a crimping jaw in accordance with the present invention.
FIG. 4C shows a third embodiment of a front profile of a crimping jaw in accordance with the present invention.
Figure 7:
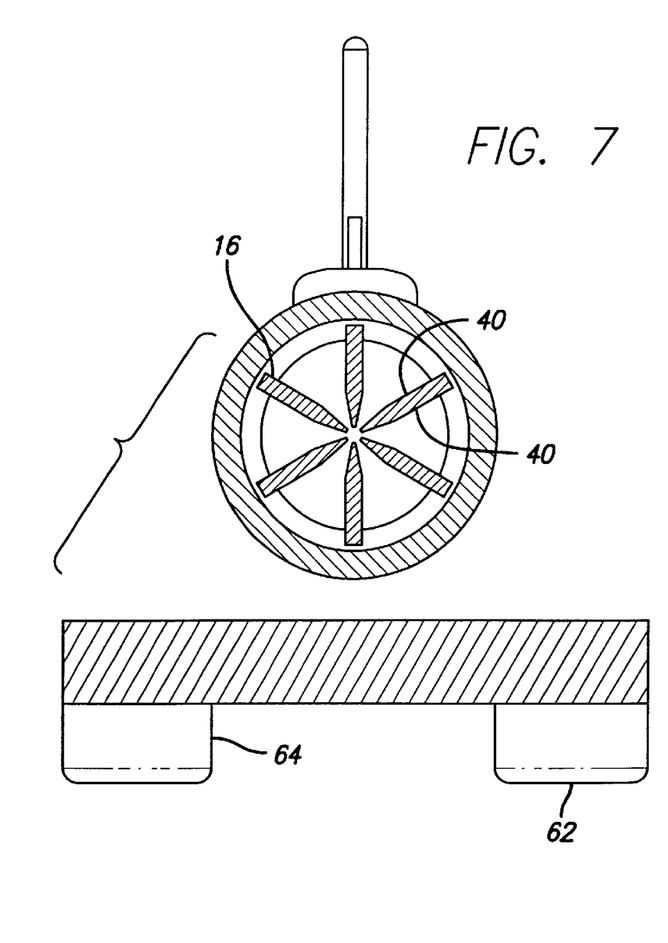
FIG. 7 is a sectional view, taken along the line 7—7, of the stent crimping device shown in FIG. 2.

The crimping jaws 16 are radially positioned about the axis of the inner hub 12 (see FIG. 7 for positioning) and include an external bearing face 36, a crimping edge 38, a pair of slide faces 40, a keyway 42 recessed into each slide face 40, and a push rod cavity 44 (FIG. 8). With reference to FIGS. 4A–4C, the crimping edge 38 has a profile 46 which may be of several configurations. The presently preferred configurations are a V-shaped edge as shown in FIG. 4A, a radiused or U-shaped edge as shown in FIG. 4B, and a rectangular configuration as shown in FIG. 4C. These profiles 46 are exemplary and are not inclusive. What is important is that the profile 46 produces a crimp which creates a region of high frictional resistance between the stent 24 and the balloon 22. The crimping edge profile 46 may vary depending upon the toughness and thickness of the balloon material. With relatively thick balloons made of strong materials, where there is less risk of the balloon bursting during inflation, caused by a sharp edge of a stent, it may be desirable to use a crimping edge which causes the stent to be crimped 24 to engage or dig into the surface of the catheter balloon 22. A V-shaped edge profile is well suited for such an application. When relatively thin balloons are to be used, it is desirable to create regions of high friction between the stent to be crimped 24 and the balloon 22 without allowing the crimped stent to dig into the balloon surface as such action may cause the balloon to burst during inflation. A radiused or U-shaped edge profile is well suited to these applications. Other profiles for the crimping edge are possible.

Figure 5A:
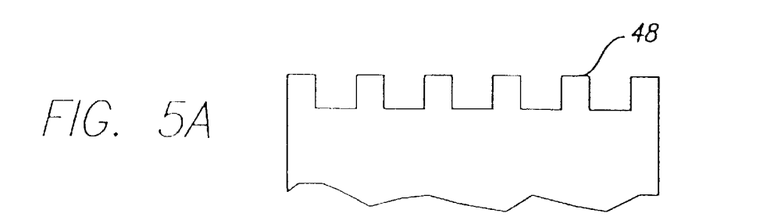
FIG. 5A shows one embodiment of a side profile of a crimping jaw in accordance with the present invention.
Figures 5B, 8:
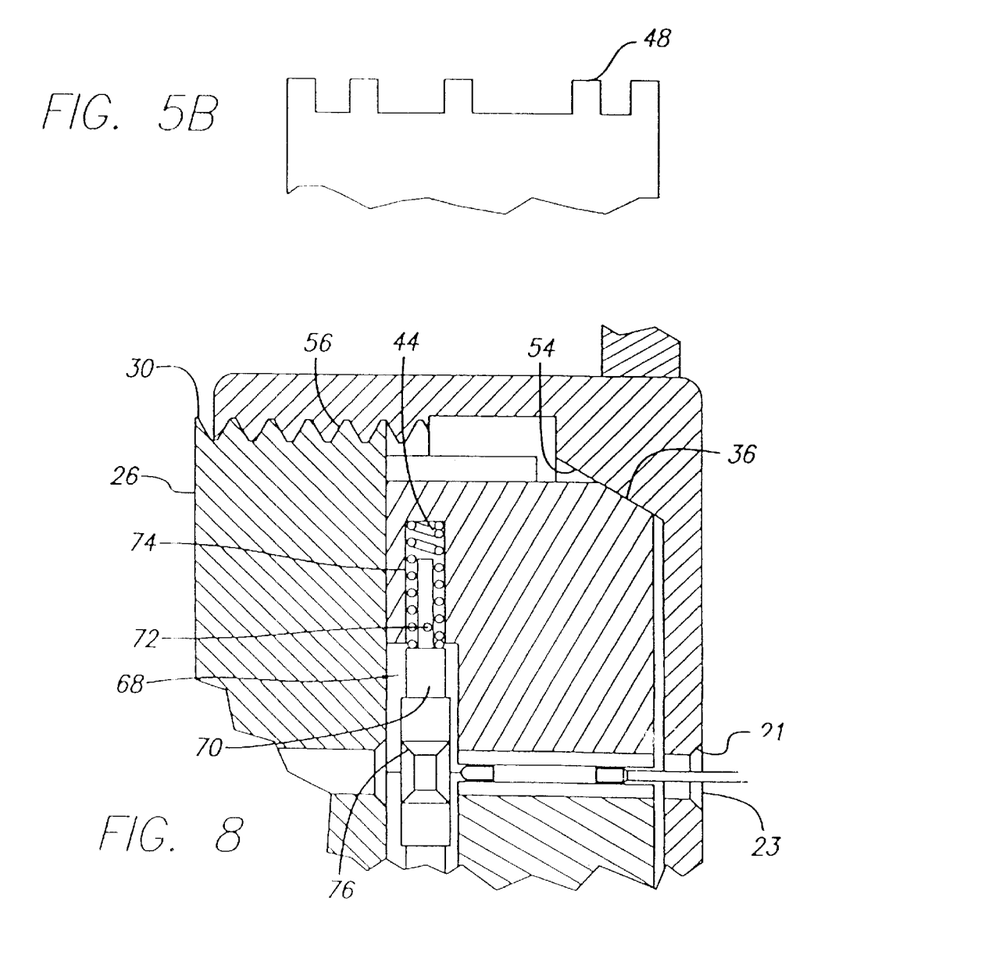
FIG. 5B shows another embodiment of a side profile of a crimping jaw in accordance with the present invention.
FIG. 8 is a partial cutaway view, enlarged in scale, of the upper half of the stent crimping device shown in FIG. 4.
Figure 9:
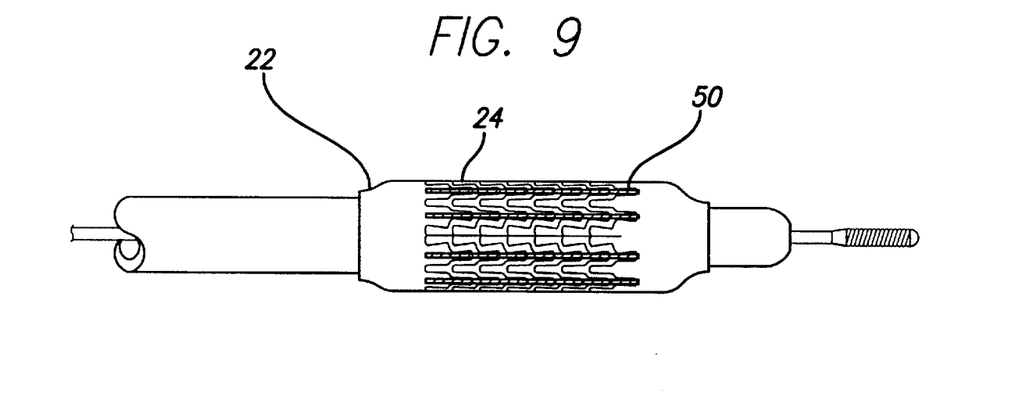
FIG. 9 is a view of a stent-delivery catheter depicting one form of stent crimp which may be produced by a stent crimping device embodying features of the present invention.
Figure 10:
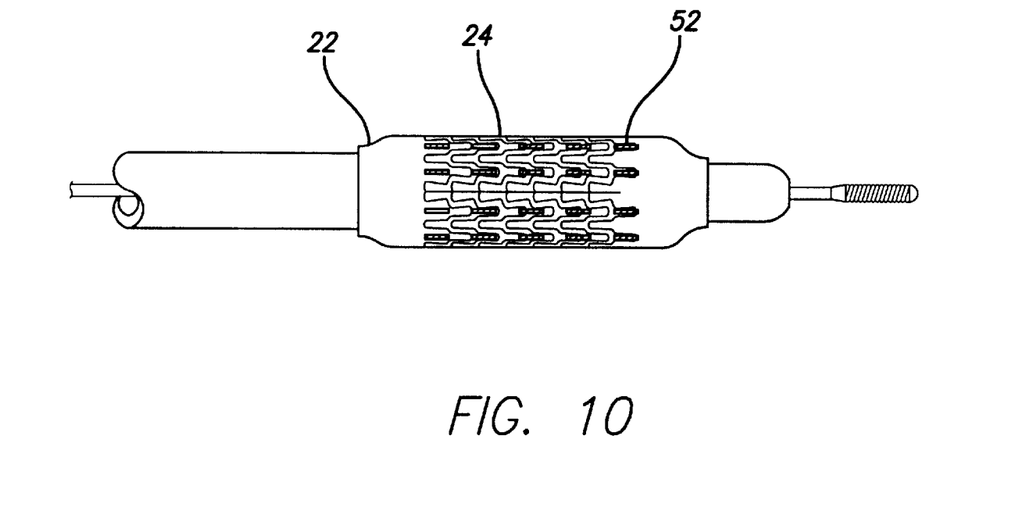
FIG. 10 is a view of a stent-delivery catheter depicting a second form of stent crimp which may be produced by a stent crimping device embodying features of the present invention.

The length of the crimping edge 38 may be continuous as shown in FIG. 3 or the crimping edge 38 may be formed with a plurality of protrusions 48, which form a discontinuous crimping edge as shown in FIGS. 5A and 5B. The plurality of protrusions 48 may be equally spaced (FIG. 5A) or the protrusions may be spaced in a selected pattern (FIG. 5B). The continuous crimping edge is used to produce crimps which form a plurality of straight grooves 50 in the stent 24, as is shown in FIG. 9. The discontinuous edge is used to produce crimps which form a plurality of radial indentations 52 in the stent 24, as is shown in FIG. 10. The radial indentations 52 correspond to the pattern of the crimping edge 38 and may be uniformly spaced or non-uniformly spaced about the body of the stent.

Figure 6:
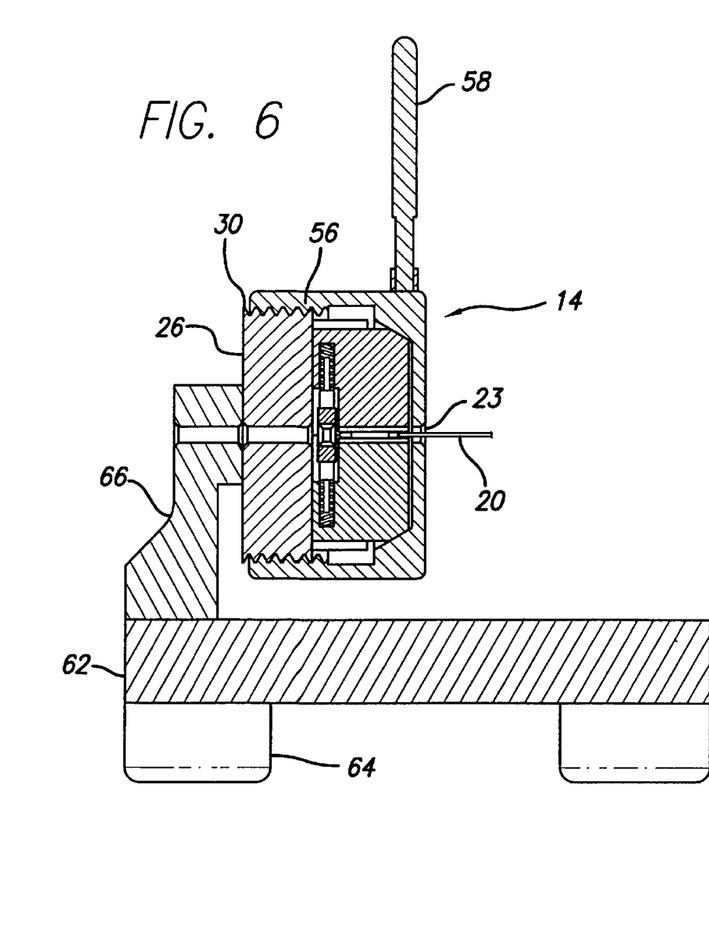
FIG. 6 is a sectional view, taken along the line 6—6, of the stent crimping device shown in FIG. 1.

Referring now to FIGS. 3, 6, and 8, the outer hub 14 is formed as a thin walled cylindrical cover which encloses the crimping jaws 16 and is rotatable about the inner hub 12. The outer hub 14 includes an internal bearing face 54 (best seen in FIG. 8), which interfaces with the external bearing faces 36 of the crimping jaws 16. The external hub 14 also includes an internal power screw thread 56 for engagement with the external power screw thread 30 of the inner hub 12. Additionally included are the aperture 23 for receipt of the stent delivery system 20, and an operating handle 58 for imparting rotary motion to the outer hub 14. The aperture 23 has a generally circular cross section and may have a slightly tapered entrance section 21 (best seen in FIGS. 3 and 4) for guiding the stent-carrying catheter 20 into the crimping device 10. Other shapes may be used if desired to accommodate other stent cross sections.

The inner hub 12, crimping jaws 16, and outer hub 14 may be made of any suitable material such as steel, aluminum, and various structural plastics. Portable versions of the tool, which are intended for on-site crimping of stents 24 to balloon catheters 20 at medical clinics, can be made from lightweight structural plastics to reduce the weight of the device. In addition, for on-site clinical use, it may be beneficial to utilize a transparent plastic, such as transparent acrylic resin, to allow for easy observation of the position of the stent 24 in relation to the crimping jaws 16. Conversely, it may be beneficial to produce versions of the tool intended for high volume production from more durable materials such as aluminum and steel.

Components of the device which are made from plastic materials may be produced by injection molding techniques and fastened by adhesive bonding, ultrasonic welding, other suitable bonding methods, or by mechanical fasteners. Components of the device which are made from metallic materials may be produced by any conventional machining or casting technique and may be attached by welding, mechanical fasteners, or other suitable methods.

Referring now to FIGS. 1 and 2, the base assembly 18 includes a base plate 62, supporting feet 64, and an adapter arm 66. In the embodiment shown in the figures, the base plate 62 is a flat square plate with chamfered corners. The supporting feet 64 are of cylindrical configuration and the adapter arm 66 is of an L-configuration. The supporting feet 64 are attached to the base plate 62 which is rigidly attached to the adapter arm 66. The adapter arm 66 is attached to and supports the inner hub assembly 12. The components of the base assembly 18 may be made of any suitable material such as steel, aluminum, and various structural plastics. The components of the base assembly 18 may be interconnected by any known means including mechanical fasteners, welding, and structural adhesives. The particular embodiment of the base assembly described is exemplary only. The base assembly may have any configuration which provides firm support for the hub assemblies. As will be understood by those skilled in the art, the configuration of the base assembly 18 will vary depending on the intended application. For example, a stent crimping device 10 intended for on-site use in a medical clinic will likely have a different base assembly than that of a device intended for use in volume production of pre-crimped stent-delivery catheters.

With reference now to FIGS. 3–8, one particular embodiment of the stent crimping device 10 of the present invention can be assembled as follows. The inner hub 12 is rigidly fixed to the adapter arm 66 of the base assembly 18. The slide blocks 28 are spaced on the cylindrical disk 26 so as to hold the crimping jaws 16 in the desired arrangement. The guide rails 34 of the slide blocks 28 are slidably engaged by the keyways 42 of each crimping jaw 16. Thus, the crimping jaws 16 are free to translate radially inwardly or outwardly, but are otherwise retained by the slide blocks 28 of the inner hub 12. Six crimping jaws 16 are shown evenly spaced on the inner hub 12 (FIG. 7) in order to provide evenly spaced grooved crimps. However, this construction is meant to be exemplary only. The number of crimping jaws 16 may be either more or less than six and the spacing may be non-uniform.

With particular reference to FIG. 8, each push rod cavity 44 in each crimping jaw 14 is loaded with a spring-loaded push rod assembly 68. The push rod assembly 68 includes a push rod 70 which incorporates a spring guide 72, and a spring 68. The push rod assembly 70 abuts a push rod stop 76, which may be a separate component or may be formed as an integral part of the inner hub 12. The spring-loaded push rod assembly 68 biases the crimping jaws 16 radially outward from the stent to be crimped 24.

Referring again to FIGS. 3–8, the outer hub 14 is rotatably attached to the inner hub 12 by means of the respective power screw threads 30 and 56, with the external power screw thread 30 of the inner hub 12 engaging the matching internal power screw thread 56, of the outer hub 14. The outer hub 14 may translate axially inwardly or outwardly by rotating over the fixed inner hub 12. The outer hub 14 is attached to the inner hub 12 by rotating the outer hub clockwise so that it translates axially inwardly until the internal bearing face 54 of the outer hub 14 contacts the internal bearing faces 36 of the crimping jaws 16.

The stent crimping device 10 functions as follows. Once the internal bearing surface 54 of the outer hub 14 is seated against the mating surfaces 36 of the crimping jaws 16, the crimping device 10 is ready for use. An operator need only position a stent 24 over the inflation balloon 22 of a stent delivery system 20 and insert the stent delivery system 20 through the aperture 23 between the crimping jaws 16. In embodiments of the device 10 which are made of clear plastic, this procedure is aided by visual observation of the position of the stent delivery system. Once the stent 24 is in position, the operator need only grasp the handle 58 and rotate the handle clockwise until further rotation is prevented by the push rod stop 76.

After the bearing surfaces 54 and 36 have made initial contact, additional rotation of the outer hub 14, via the handle 58, produces additional inward translation of the internal bearing face 54, which acts against the external bearing face 36 of the crimping jaws 16 to produce a radially inwardly acting reaction force at each jaw 16. The radially inwardly acting reaction forces cause the bearing surfaces 36 of the crimping jaws 16 to slide radially inward along the bearing surface 54 of the outer hub 14, and thereby the crimping jaws 16 move radially inwardly against the stent to be crimped 24. Once the jaws 16 contact the stent 24, a small amount of additional rotation via the handle 58 causes the jaws 16 to crimp the stent 24. In addition, the radially inward translation of the crimping jaws 16 causes the spring-loaded push rod 70 to translate axially inwards until the spring guide 72 bottoms out inside the push rod cavity 44. The maximum radially inward movement of the crimping jaws 16 may be limited by the travel of the push rod spring guide 72. The length of the push rod spring guide 72 may be selected so that the push rod assemblies 68 bottom out after a selected amount of crimping jaw movement. In this manner, a controlled uniform degree of force may be applied to the stent to be crimped 24. Those skilled in the art will realize that other push rod designs are possible as are other methods of limiting the allowable outer hub rotation, such as incorporating stops on the inner hub 12. When the push rod spring guides 72 contact the top of the push rod cavity 44, further rotation of the handle 58 is prevented, thereby the operator will know that the crimping operation is completed. At this point the operator rotates the handle 58 counter clockwise thereby causing the outer hub 12 to translate axially outwardly. As the outer hub rotates axially outwardly, the spring-loaded push rod assemblies 68 bias the crimping jaws 16 away from the stent 24, thereby allowing the stent delivery system to be removed from crimping device 10.

The power screw threads 30 and 56 may be of any suitable thread type, such as the widely used Acme and square thread designs. The outer hub translates either axially inwardly or outwardly during clockwise rotation. This movement is dependant on whether the power screw thread follows the common right hand thread convention or the less common left hand thread convention. The above example assumes the power screw threads follow the common right hand thread convention. However, the principle of operation is the same regardless of the choice of thread type or thread convention.

It will be appreciated that a new stent crimping device has been presented. The crimping device is capable of producing crimps consisting of a plurality of longitudinal grooves or a plurality of radial indentations. Either type of crimp creates regions of high frictional resistance between the stent and the catheter balloon, thereby improving stent security on the catheter balloon. While only the presently preferred embodiment has been described in detail, as will be apparent to those skilled in the art, modifications and improvements may be made to the device and method disclosed herein without departing from the scope of the invention. Accordingly, it is not intended that the invention be limited, except as by the appended claims.

What is claimed is:

1. A stent crimping device for crimping a stent onto a balloon catheter comprising:
   a plurality of jaws radially spaced about a longitudinal axis and capable of moving radially inwardly and outwardly with respect to the longitudinal axis, the jaws being spaced radially outwardly from the longitudinal axis a sufficient distance to receive within the jaws a stent-carrying balloon catheter, each jaw having an edge for crimping a stent;
   an inner hub and outer hub, the inner hub having a longitudinal axis, and including retention means for retaining the plurality of jaws in a selected radial pattern about the longitudinal axis, the outer hub enclosing the jaws and being rotatably attached to the inner hub such that the outer hub translates axially on the longitudinal axis when rotated about the inner hub;
   force application means for moving the jaws radially inwardly toward the longitudinal axis to compress and crimp the stent against the balloon catheter to form a unitary stent-delivery catheter; and
   a plurality of spring-loaded push rod assemblies, the assemblies being received in cavities in the jaws and bearing against stops on the inner hub to allow the stent-bearing catheter to be removed from the jaws.

2. The stent crimping device of claim 1, wherein the force application means comprises an angled bearing face on each jaw which contacts a mating angled bearing face within the outer hub, wherein rotation of the outer hub causes the bearing face in the outer hub to translate axially against the bearing faces on the jaws forcing the jaws to translate radially inwardly.

3. The stent crimping device of claim 1, further including a base assembly, wherein the base assembly supports the crimping device by attachment to the inner hub.

4. The stent crimping device of claim 1, wherein the outer hub is rotatably attached to the inner hub by means of mating screw threads in the inner and outer hubs respectively.

5. The stent crimping device of claim 1, wherein the outer hub includes an aperture for guiding a stent-carrying balloon catheter within the jaws.

6. The stent crimping device of claim 1, wherein the retention means for retaining the jaws within the inner hub comprise keyways in the jaws and mating guide rails on the inner hub.

7. The stent crimping device of claim 1, wherein the crimping edge of the jaws includes a profile selected from the group consisting of V-shaped, U-shaped, and rectangular profiles.

8. The stent crimping device of claim 1, wherein the jaws are equally spaced about the longitudinal axis.

9. The stent crimping device of claim 1, wherein the crimping edge is continuous along its length.

10. The stent crimping device of claim 1, wherein the crimping edge is discontinuous along its length, the edge comprising a plurality of protrusions.

11. The stent crimping device of claim 10, wherein the plurality of protrusions are equally spaced.

12. The stent crimping device of claim 10, wherein the plurality of protrusions are spaced in a selected pattern.

13. A stent crimping device for crimping a stent onto a balloon catheter, the device comprising:
   a plurality of jaws radially spaced about a longitudinal axis and capable of moving radially inwardly and outwardly with respect to the longitudinal axis, the jaws being spaced radially outwardly from the longitudinal axis a sufficient distance to receive within the jaws a stent-carrying balloon catheter, each jaw having an angled bearing face and an edge for crimping a stent;
   an inner hub including retention means for retaining the plurality of jaws in a selected radial pattern about the longitudinal axis;
   an outer hub enclosing the jaws and including an angled bearing surface slidably engaged with the angled bearing surface of the jaws;
   the outer hub being rotatably attached to the inner hub in such manner that the outer hub translates axially along the longitudinal axis when rotated about the inner hub, wherein rotation of the outer hub causes the bearing face in the outer hub to translate axially against the bearing faces on the jaws forcing the jaws to translate radially inwardly, wherein the jaws compress and crimp a stent; and
   a plurality of spring-loaded push rod assemblies, the assemblies being received in cavities in the jaws and bearing against stops on the inner hub to allow the stent-bearing catheter to be removed from the jaws.

14. The stent crimping device of claim 13, wherein the outer hub is rotatably attached to the inner hub by means of mating screw threads in the inner and outer hubs respectively.

15. The stent crimping device of claim 13, wherein the outer hub includes an aperture for guiding a stent-carrying balloon catheter within the jaws.

16. The stent crimping device of claim 13, wherein the retention means for retaining the jaw within the inner hub comprise keyways in the jaws and mating guide rails on the inner hub.

17. The stent crimping device of claim 13, wherein the crimping edge of the jaws includes a profile selected from the group consisting of V-shaped, U-shaped, and rectangular profiles.

18. The stent crimping device of claim 13, wherein the jaws are equally spaced about the longitudinal axis.

19. The stent crimping device of claim 13, wherein the crimping edge is continuous along its length.

20. The stent crimping device of claim 13, wherein the crimping edge is discontinuous along its length, the edge comprising a plurality of protrusions.

\* \* \* \* \*

UNITED STATES PATENT AND TRADEMARK OFFICE
CERTIFICATE OF CORRECTION

PATENT NO.    : 6,510,722 B1
DATED         : January 28, 2003
INVENTOR(S)   : Denise Ching et al.

It is certified that error appears in the above-identified patent and that said Letters Patent is hereby corrected as shown below:

<u>Title page,</u>
Item [57], ABSTRACT,
Line 3, change "resistence", to read -- resistance --.

Signed and Sealed this

Fifteenth Day of April, 2003

JAMES E. ROGAN
*Director of the United States Patent and Trademark Office*